(12) United States Patent
Hino et al.

(10) Patent No.: US 7,973,021 B2
(45) Date of Patent: Jul. 5, 2011

(54) IMMUNOMODULATING AGENT IN GUT

(75) Inventors: Keiko Hino, Okayama (JP); Mayumi Kurose, Okayama (JP); Takeo Sakurai, Okayama (JP); Shinichiro Inoue, Okayama (JP); Tohru Ogawa, Okayama (JP); Kazuyuki Oku, Okayama (JP); Hiroto Chaen, Okayama (JP); Shigeharu Fukuda, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 495 days.

(21) Appl. No.: 12/067,577

(22) PCT Filed: Sep. 15, 2006

(86) PCT No.: PCT/JP2006/318390
§ 371 (c)(1),
(2), (4) Date: Mar. 20, 2008

(87) PCT Pub. No.: WO2007/034748
PCT Pub. Date: Mar. 29, 2007

(65) Prior Publication Data
US 2010/0143389 A1 Jun. 10, 2010

(30) Foreign Application Priority Data
Sep. 22, 2005 (JP) .................. 2005-275360

(51) Int. Cl.
*A01N 43/04* (2006.01)
*A61K 31/715* (2006.01)

(52) U.S. Cl. ........................................ 514/54

(58) Field of Classification Search .................. None
See application file for complete search history.

(56) References Cited

U.S. PATENT DOCUMENTS
2006/0276432 A1* 12/2006 Oku et al. .................. 514/61

FOREIGN PATENT DOCUMENTS

| | | |
|---|---|---|
| EP | 1229112 A1 | 8/2002 |
| EP | 1284286 A1 | 2/2003 |
| EP | 1350509 A1 | 8/2003 |
| EP | 1541660 A1 | 6/2005 |
| JP | 5178876 A1 | 7/1993 |
| JP | 200060541 A1 | 2/2000 |
| JP | 325555 A1 | 11/2002 |
| JP | 2003522784 A1 | 7/2003 |
| WO | 01 60346 A2 | 8/2001 |
| WO | 01/090338 A1 | 11/2001 |
| WO | 0100361 A1 | 2/2002 |
| WO | 02/38146 A1 | 5/2002 |
| WO | 2004/020552 A1 | 3/2004 |

OTHER PUBLICATIONS

G. L. Cote, Enzymically produced cyclic x-1,3-linked and x-1,6 linked oligosaccharides of D-glucose (1994), vol. 226 pp. 641-648.
J. Appl. Glycosci.,vol. 52 Suppl., 36 (2005) B3a-2.
J. Appl. Glycosci., 52, Suppl., 36 (2005) B3a2.

\* cited by examiner

*Primary Examiner* — Traviss C McIntosh, III
(74) *Attorney, Agent, or Firm* — Browdy and Neimark, PLLC

(57) ABSTRACT

An object of the present invention is to provide an immunomodulating agent in gut that can be ingested continuously in daily diet without adverse side effect. The object is attained by providing an immunomodulating agent in gut comprising a cyclic tetrasaccharide as an effective ingredient.

5 Claims, No Drawings

IMMUNOMODULATING AGENT IN GUT

TECHNICAL FIELD

The present invention relates to an immunomodulating agent in the gut, in particular, an immunomodulating agent in the gut comprising a cyclic tetrasaccharide.

BACKGROUND ART

Higher organisms including humans have a gut immune function to prevent infections with pathogens such as bacteria, viruses and parasites, and production of various kinds of antibodies and cytokines are properly regulated in the gut. Particularly, immunoglobulin A (IgA) is a very important factor in gut immune system. In recent years, oral infections diseases tend to decrease as the living environment is cleaner. However, since secretion of IgA tends to decrease, it is feared that susceptibility of serious infection diseases increases with compromised gut immunity.

For a method of modulating gut immunity, International Patent Publication WO02/038146 discloses that trehalose, a kind of saccharide, has the regulatory effect of producing IgA and interferon-γ (IFN-γ) by acting on Peyer's patch cells. Japanese Patent Kokai 325555/2002 discloses that nigerooligosaccharides can prevent compromised immune function caused by nutritional disorders. However, these effects are insufficient. On the other hand, the cyclic tetrasaccharide disclosed in G. L. Cote, European Journal of Biochemistry, Vol. 226, 641-648 (1994) is not known for a function of modulating gut immunity at all.

DISCLOSURE OF INVENTION

An object of the present invention is to provide an immunomodulating agent in the gut, which can be continuously ingested in the daily diet without any adverse side effect.

As a result of the study by the inventors of the present invention, novel findings revealed that oral ingestion of cyclic tetrasaccharide assists the IgA production in the gut, that the effect is exerted on Payer's patch cells, which are gut immune tissue, and that cyclic tetrasaccharides are effective in regulating allergies by inducing IFN-γ production without inducing interleukin-4 (IL-4) production from Payer's patch cells. The present invention was accomplished by finding out that the enteric environment of the animals ingesting cyclic tetrasaccharide is improved so that it is easy to increase lactic acid bacteria.

The present invention attains the above object by providing an immunomodulating agent in the gut comprising a cyclic tetrasaccharide.

The present invention is effective in preventing infections or allergies by modulating gut immunity. The immunomodulating agent in the gut of the present invention can be continuously ingested in the daily diet without any adverse side effect.

BEST MODE FOR CARRYING OUT THE INVENTION

The cyclic tetrasaccharide as an effective ingredient in the immunomodulating agent in the gut of the present invention is a non-reducing saccharide having the structure of cyclo{>6)-α-D-glucopyranosyl-(1>3)-α-D -glucopyranosyl-(1>6)-α-D-glucopyranosyl-(1>3)-α-D -glucopyranosyl-(1>}. This saccharide can be produced from starch by an enzymatic method disclosed in International Patent Publications such as WO02/10361. The form of the saccharide can be selected from syrups, crystalline powders containing syrup, hydrous crystals, anhydrous crystals, amorphous solids. Any content of the cyclic tetrasaccharide in the immunomodulating agent in gut of the present invention is acceptable as long as it exerts modulating gut immunity when administered to animals including humans, normally 1 to 100 w/w %, preferably 10 to 100 w/w %, more preferably 20 to 100 w/w %, on a dry solid basis.

The action mechanism of the mucosal immunomodulating agent of the present invention is explained as follows. Since the cyclic tetrasaccharide orally administered to humans or animals is not digested in the stomach or the gut, the cyclic tetrasaccharide directly stimulates Peyer's patch cells, which are gut immune tissue. As a result, the gut immune function is enhanced by accelerating production of IgA or cytokines that accelerate IgA production, such as interleukin-6 (IL-6) or transforming growth factor-β (TGF-β). Since the cyclic tetrasaccharide accelerates IFN-γ production without accelerating IL-4 production on Payer's patch cells, it regulates allergies by making Th1 dominant in Th-balance. Also, the cyclic tetrasaccharide is metabolized by lactic acid bacteria in the gut as an energy source, resulting in increasing the number of lactic acid bacteria and activating the lactic acid bacteria. The immunomodulating agent in gut of the present invention, comprising the cyclic tetrasaccharide as an effective ingredient, is thought to improve the enteric environment and modulate gut immunity under normal conditions.

Although the mucosal immnomodulating agent of the present invention can be the cyclic tetrasaccharide itself, the agent can be a composition comprising the cyclic tetrasaccharide as an effective ingredient, such as a foods and drinks, medical products, quasi-drugs, health foods, feeds and baits. As the composition, it can contain substances acceptable in the above forms, such as water, alcohols, starches, proteins, dietary fibers, saccharides, lipids, vitamins, minerals, flavoring agents, coloring agents, sweeteners, seasonings, spices, stabilizers, antioxidants, antiseptics. Particularly, the following substances can be contained: proteins such as lactoferrin, casein, collagen and soy protein and their decomposed matters; flavonoids such as lutin, hesperidin, quercetin and isoflavon and their glycosides; calcium salts such as calcium lactate and calcium glycerophosphate; vitamins such as vitamin A, vitamin B1, vitamin B2, vitamin B6, vitamin B12, vitamin C, vitamin D and vitamin E and their derivatives; saccharides such as maltose, trehalose, maltosyl trehalose, lactosucrose, nigerose, isomaltose, nigerooligosaccharides, isomaltooligosaccharides and cyclodextrins; amino sugars such as glucosamine, galactosamine and mannosamine; glycosaminoglycans such as hyaluronic acid, chondriotin sulfate and heparan sulfate; sugar alcohols such as sorbitol and maltitol; hormones such as calcitonin, estrogen and protein anabolic hormones; photosensitizing dyes such as "KANKOSO 101", "KANKOSO 201", "KANKOSO 301" and "KANKOSO 401", plants, fungi, or their extracts such as indigo plant, perilla, chinese parsley, pfaffia, "Rokkakureishi" (*Ganoderma lucidum*), Agarics and Mesimakobu; bifidobacteria-growth saccharides; powdery milk; shell meal; coral meal; propolis extract; royal jelly; honey and L-ascorbic acid 2-glucoside.

Since the immunomodulating agent in the gut of the present invention modulates gut immunity, it can be used for prevention and treatment of diseases caused by viruses such as hepatitis A virus, polio virus and rotavirus diseases caused by bacteria such as cholera vibrio, dysentery bacillus, typhoid bacteria, *Salmonella, Campyrobacter*, melioidosis bacteria, *Vibrio parahaemolyticus, Brucella* and coliform bacillus 0-157; diseases caused by parasites such as broad tapeworm, "Yokogawakyuchu" (*Metagonimus yokogawai*), liver flukes, *Echinostomida*, lung flukes, *Anisakis, Gnathostomiasis, Angiostrongylus cantonensis, Entamoeba histolytica, Cryptosporidium, Plasmodium* and microfilaria; or allergies such as food allergies and pollen allergy. The immunomodulating agent in the gut of the present invention can be administered or ingested at a dose of 0.001 to 5 g/kg-body weight, preferably 0.01 to 2 g/kg-body weight, the more preferably 0.1 to 2 g/kg-body weight a day. When the dose is under 0.01 g/kg-body weight, the desired effect is not exerted. When the dose is over 5 g/kg-body weight, it is not preferred because of the quantitative difficulty of ingesting and the possibility of causing diarrhea.

The following experiments explain the present invention.

EXPERIMENT 1

Immunomodulating Effect in Gut on Mice Ingesting Saccharides (Analysis of Feces)

To investigate immunomodulating effects of various saccharides, IgA contents in feces of mice administered saccharides were measured. After six-week-old female BALB/c mice were preliminarily grown for a week with AIN-93G, which is a standard growth purified diet for nutritional study using mice or rats introduced by American Institute of Nutrition in 1993, they were separated in groups of five mice each, and unlimitedly administered the test diets, which is made by supplementing 5 w/w % of the cyclic tetrasaccharide (produced in Example 2), 5 w/w % of nigerooligosaccharide (12.5 w/w % of "NISSHOKU TASTE OLIGO SYRUP", containing 40% or more of nigerooligosaccharide on a dry solid basis, commercialized by Nihon Shokuhin Kako Co., Ltd.), or 5 w/w % of isomaltooligosaccharide ("ISOMALT 90" commercialized by Hayashibara Shoji, Inc.) to the same formula diet described above except the amount of corn starch was reduced by the relevant weight of the added test saccharide. As control, one group was administered with the standard growth purified diet (AIN-93G) without the test saccharides described above. After 1, 2, 3 and 4 weeks from the initial administration of the test or control diets, fresh feces were taken from each mouse and IgA content was measured by the ELISA method using anti-IgA antibody (MOUSE IgA ELISA QUANTITATION KIT produced by Bethyl Laboratories, Inc). The average values calculated from the data of five mice were shown in Table 1. The values expressed in percent in Table 1 mean the relative amounts with respect to control in each week.

TABLE 1

| | IgA content (mg/g) | | | |
| --- | --- | --- | --- | --- |
| Saccharides | First week (Age in 8 weeks) | Second week (Age in 9 weeks) | Third week (Age in 10 weeks) | Fourth week (Age in 11 weeks) |
| Control | 5.27 | 3.96 | 2.19 | 2.16 |
| Cyclic tetrasaccharide | 5.61 106% | 8.47 214% | 7.57 346% | 7.09 328% |
| Isomalto-oligosaccharide | 8.87 168% | 6.67 168% | 3.33 152% | 3.11 144% |
| Nigero-oligosaccharide | 4.73 90% | 4.79 121% | 2.47 113% | 2.13 99% |

As is evident from Table 1, on the mice bred on control purified diet, a decrease of IgA content in feces was observed along with the length of the breeding period (age in weeks). This phenomenon is thought to be caused by compromised gut immunity function resulting from decreased oral ingestion of antigens because of feeding on the purified clean diet. On the other hand, it was found that the cyclic tetrasaccharide among the test saccharides added in the purified diet increased IgA contents in feces of the mice and high levels of IgA secretion was maintained even as the mice were continuously fed the purified clean diet.

EXPERIMENT 2

Immunomodulating Effect in Gut on Mice Ingesting the Saccharides (Analysis of Cecal Contents)

To investigate the immunomodulating effect of the various saccharides, IgA content and IgG content in the cecal contents of the mice administered saccharides were measured. After the mice fed on the purified diet containing the test saccharide or the control purified diet (AIN-93G) for 4 weeks in Experiment 1 were killed, their cecums were surgically removed. After the pH and weight of the cecum contents were measured, IgA content and IgG content in the cecal contents were measured. IgA content was measured by ELISA method using anti-IgA antibodies and IgG content was measured by ELISA method using anti-IgG antibodies (MOUSE IgG ELISA QUANTITATION KIT produced by Bethyl Laboratories, Inc) and the amounts of the antibodies per gram of the cecal contents were obtained. The results were shown in Table 2.

TABLE 2

| Saccharide | pH | Weight (mg) | IgA content (mg/g) | IgG content (mg/g) |
| --- | --- | --- | --- | --- |
| Control | 7.73 | 128 | 1.9 | 80 |
| Cyclic tetrasaccharide | 7.16 | 169 | 4.4 | 85 |
| Isomaltooligo-sacchharide | 7.79 | 86 | 3.7 | 56 |
| nigerooligo-saccharide | 7.89 | 100 | 3.5 | 77 |

As is shown in Table 2, it was suggested that the cyclic tetrasaccharide brought a change in the intestinal flora from the decrease of the cecal pH and the increase of the amount of the cecal contents. The test saccharides increased the IgA contents and did not bring significant changes of the IgG contents. Since the cyclic tetrasaccharide among the test saccharides brought the highest increase of the IgA content, it was found that the cyclic tetrasaccharide enhances gut immunity by preferential increase of IgA content.

EXPERIMENT 3

Immunomodulating Effect in Gut on Mice Ingesting the Saccharides (Analysis of Peyer's Patch Cell)

To investigate the immnomodulating effect of the various saccharides, the contents of IgA, IL-6 and TGF-β produced by the Peyer's patch cells taken from the mice administered the saccharides. After the Peyer's patches taken from the mice administered with the purified diet containing the test saccharides or the control purified diet in Experiment 2 were cut by scissors, they were treated in 0.2 w/w % collagenase solution at 37° C. for 30 minutes. They were filtered through a cell strainer and the filtrate containing the cells were centrifuged to give the cell precipitates. They were suspended in 45 w/w % PARCOR (commercialized by Amersham, PLC), the cell suspensions were layered on 75 w/w % PARCOR and centrifuged for 10 minutes at 1,000 g. Cells floating at the interface between 45 w/w % PARCOR and 75 w/w % PARCOR were collected and suspended in RPM1164 medium containing 10% FCS and 10 mM HEPES to give the cell suspensions at a concentration of $1\times10^6$ cells/ml. They were seeded in 24-well microplates by 1 ml/well, added with 2 µg/m1 of concanavalin A, and cultured at 37° C. for 48 hours in atmosphere of 5% carbon dioxide. The culture supernatant was collected from each well and their IgA contents, TGF-β contents or IL-6 contents were measured by ELISA method using anti-mouse-IgA antibody, anti-mouse-IL-6 antibody and anti-mouse-TGF-µ1 antibody, then the averages were calculated from the data of five mice. The results were shown in Table 3. The values in Table 3 means relative amounts (%) to IgA, IL-6 or TGF-β amount produced in Peyer's patch cells taken from the control mice.

TABLE 3

| Saccharide | Relative IgA content (%) | Relative IL-6 content (%) | Relative TGF-β content (%) |
|---|---|---|---|
| Cyclic tetrasaccharide | 209 | 326 | 142 |
| Isomaltooligo-sacchharide | 77 | 200 | 147 |
| nigerooligo-saccharide | 77 | 126 | 77 |

As is shown in Table 3, the cyclic tetrasaccharide increased IgA secretion in Peyer's patch cells. It increased also production of IL-6 and TGF-β, which are cytokines inducing IgA production. These results reveal that the cyclic tetrasacharide has an effect in accelerating IgA secretion on Peyer's patch cells.

EXPERIMENT 4

Measurement of the Amounts of Various Organic Acids in Cecal Contents of Mice Ingesting the Saccharides To investigate the effects of the various saccharides on the enteric environment of mice, the contents of organic acids in the cecal contents were measured. After the cecal contents taken from the mice administered the purified diet containing the test saccharides or the control purified diet in Experiment 2 were suspended in an adequate amount of purified water, their supernatants collected by centrifugation were filtered with membrane (pore size of 0.45 µm). The filtrates were subjected to an ion chromatoanalyzer IC500P (produced by Yokogawa Electric Corporation) loaded with precolumn PCS5-052 and separation column SCS5-252, and eluted with 2 mM sulfuric acid (1.0 ml/min) to analyze the amounts of organic acids. The results obtained as the molar concentrations per gram of the cecal contents were shown in Table 4. The values expressed in percent in Table 4 mean the relative amounts of each organic acid in the cecal contents to those of the control mice.

TABLE 4

| | Amount of organic acid (µmol/g) | | | |
|---|---|---|---|---|
| Organic acid | Control | Cyclic tetrasaccharide | Isomaltooligo-saccharide | Nigerooligo-saccharide |
| Malic acid | 0.84 | 1.5 (179%) | 0.80 (95%) | 1.1 (131%) |
| Succinic acid | 2.1 | 5.6 (267%) | 2.1 (100%) | 2.2 (105%) |
| Lactic acid | 0.42 | 4.2 (1000%) | 1.0 (238%) | 1.7 (405%) |
| Formic acid | 0.33 | 0.82 (258%) | 0.39 (118%) | 0.96 (291%) |
| Acetic acid | 67 | 63 (94%) | 46 (69%) | 42 (63%) |
| Propionic acid | 12 | 12 (100%) | 6.8 (57%) | 6.3 (53%) |

TABLE 4-continued

| | Amount of organic acid (µmol/g) | | | |
|---|---|---|---|---|
| Organic acid | Control | Cyclic tetrasaccharide | Isomaltooligo-saccharide | Nigerooligo-saccharide |
| Isobutyric acid | 2.7 | 1.9 (70%) | 0.50 (19%) | 0.90 (33%) |
| n-Butyric acid | 6.8 | 14 (206%) | 7.3 (107%) | 7.0 (103%) |
| Isovaleric acid | 3.3 | 2.4 (73%) | 1.6 (48%) | 1.6 (48%) |
| n-Valeric acid | 1.2 | 0.87 (73%) | 1.1 (92%) | 1.1 (92%) |
| Total organic acids | 97 | 106 (109%) | 68 (70%) | 65 (67%) |

As is shown in Table 4, it was found that the test saccharides are effective in increasing lactic acid bacteria because they have the effect of increasing lactic acid content. Particularly, the cyclic tetrasaccharide increased the lactic acid content especially, as well the contents of butyric acid, succininc acid, formic acid and malic acid, resulting in increasing the total organic acids.

EXPERIMENT 5

Effects of Various Saccharides on Peyer's Patch Cells in vitro

To investigate direct effects of various saccharides on Peyer's patch cells, the amounts of IFN-γ and IL-4 produced in Peyer's patch cells taken from mice by adding various kinds of saccharide in an in vitro experiment. After six-week-old female BALB/c mice were preliminarily grown for a week with a standard growth purified diet (AIN-93G), their Peyer's patch cells were collected according to the method of Experiment 3. The cell suspension at a concentration of $1\times10^6$ cells/ml was prepared with RPMI1640 medium containing 10% FCS and 10 mM HEPES and seeded in 24-well microplates by 1 ml/well. After the test saccharides (the cyclic tetrasaccharide, nigerose or isomaltose) were added in an amount of 0.1 mg/ml and lipopolysaccharide (LPS) or concanavalin A (ConA) of 2 µg/ml, they were cultured at 37° C. for 72 hours in an atmosphere of 5% carbon dioxide. The amounts of IFN-γ in the supernatants were measured by the ELISA method using anti-mouse- IFN-γ antibodies (MURINE IFN-γELISA DEVELOPMENT KIT, produced by PeproTech, Inc.), and the amounts of IL-4 were measured by the ELISA method using anti-mouse-IL-4 antibodies (Mouse IL-4 ELISA DEVELOPMENT KIT, produced by Genzyme-Techne). As a control, the amounts of IFN-γ and IL-4 produced in Peyer's patch cells cultured with the medium without adding the test saccharides by the same way described above. These results were shown in Table 5. The values in Table 5 were shown as the relative amounts (%) to control.

TABLE 5

| | Relative amount of IFN-γ (%) | | Relative amount of IL-4 (%) | |
|---|---|---|---|---|
| Saccharide | LPS | ConA | LPS | ConA |
| Cyclic tetrasaccharie | 103 | 269 | 101 | 96 |
| Nigerose | 104 | 63 | 99 | 100 |
| Isomaltose | 100 | 53 | 97 | 100 |

As is shown in Table 5, each saccharide has no effect on IL-4 production, however IFN-γ production by stimulation of concanavalin A was accelerated by the cyclic tetrasaccharide and suppressed by nigerose or isomaltose. These results revealed that the cyclic tetrasaccharide is effective in suppressing allergies in gut.

The following examples explain the present invention in detail.

EXAMPLE 1

Immunomodulating Agent in Gut in a Syrup Form

A syrupy cyclic tetrasaccharide was prepared according to the method described in International Patent Publication WO02/10361 as follows. Potato starch suspension at a concentration of 6% was prepared and added with calcium carbonate to give a concentration of 0.1%. After adjusted at pH 6.0, the suspension was added with 0.2% of TERMAMYL 60L (an α-amylase product produced by Novo A/S) per gram of starch, on a dry solid basis, reacted at 95° C. for 10 minutes, autoclaved at 120° C. for 20 minutes, and rapidly cooled to about 35° C. to give a starch-liquefied solution of about DE4. Then, the solution was added with 0.25 ml of the concentrated solution containing α-isomaltosylglucosaccharide-forming enzyme and α-isomaltosyl-transferring enzyme per gram of starch, on a dry solid basis and reacted at pH 6.0 and 35° C. for 48 hours. The reaction mixture was heated and kept at 95° C. for 10 minutes, and filtered. The filtrate was decolorized with activated carbon, purified by desalting with H-form and OH-form ion-exchange resins, and concentrated to give a syrupy immunomodulating agent in the gut comprising 60% of cyclic tetrasaccharide. The agent, comprising 0.9% of glucose, 1.5% of isomaltose, 11.3% of maltose, 60.1% of the cyclic tetrasaccharide, and 26.2% of other saccharides, can be used as an immunomodulating agent in the gut according to the present invention.

EXAMPLE 2

Powdery Immunomodulating Agent in Gut

The syrup containing the cyclic tetrasaccharide described in Example 1 prepared according to the method described in International Patent Publication WO02/10361 was fractionated with AMBERLITE CR-1310 (Na-form) (a strongly acidic cation exchange rein produced by ORGANO Corporation).

The resin was packed in four stainless-steel columns of inside diameter of 5.4 cm with jacket, then the columns were connected in series to give the total resin-length of 20 cm. Keeping the inside temperature of the columns at 60° C., the saccharide solution of 5 v/v % of the resin was applied and fractionated by flowing water at a temperature of 60° C. at SV 0.13. The fraction containing the cyclic tetrasaccharide was collected by monitoring the saccharide composition of the eluent by HPLC and concentrated at a concentration of about 85%. The concentrate was put into a crystallizer, and cooled slowly with stirring. After adding 2% of penta-hydrated crystalline cyclic tetrasaccharie as a seed and cooled slowly, it was put into a plastic tray, and crystallized by standing at room temperature for 2 days to give a block. Then, the block was pulverized by a pulverizer to give a powdery crystalline immunomodulating agent in the gut comprising the cyclic tetrasaccharide. The agent, which is high-purity penta-hydrated crystalline cyclic tetrasaccharide with 98% purity, on a dry solid basis, can be used as an immunomodulating agent in the gut according to the present invention.

EXAMPLE 3

Health Food

After melting by heating to become soft, two parts by weight of gum base was admixed with two parts by weight of powdery maltose, four parts by weight of sucrose, one part by weight of the syrupy immunomodulating agent in the gut prepared in Example 1 comprising the cyclic tetrasaccharide, admixed with mint flavor and coloring agent. The mixture was kneaded with a roller in a conventional way and shaped to give chewing gum. Since the product has good flavor and can modulate gut immunity when orally administered, it is useful as a health food to keep or improve health.

EXAMPLE 4

Oral Liquid Health Food

The following ingredients were blended to give an oral liquid health food.

| | |
|---|---|
| The powdery crystalline immunomodulating agent in gut prepared in Example 2 comprising the cyclic tetrasaccharide | 1 part by weight |
| Skim milk | 43 parts by weight |
| Powdery whole milk | 12 parts by weight |
| Syrup | 41 parts by weight |
| Glucose | 3 parts by weight |
| Vitamin A | adequate amount |
| Vitamin D | adequate amount |
| Thiamine hydrochloride | adequate amount |
| Riboflavin | adequate amount |
| Pyridoxine hydrochloride | adequate amount |
| Cyanocobalamine | adequate amount |
| Choline bitartrate | adequate amount |
| Nicotinic-acid amide | adequate amount |
| Calcium pantothenate | adequate amount |
| Ascorbic acid | adequate amount |
| Tocopherol acetate | adequate amount |
| Iron sulfate | adequate amount |
| Calcium hydrogen phosphate | adequate amount |
| Gum arabic | adequate amount |

When this product dissolved in water was administered to patients who were restricted to ingest regular diet, modulating gut immunity and recovery of the patients can be expected as well as nutritional supports.

EXAMPLE 5

Health Food

After mixing the following ingredients homogeneously, the mixture was made into tablet by a tableting machine mounted with a pestle of diameter of 6 mm to give a tablet of 200 mg. This product has good flavor and can be used as a health food to keep or improve health by modulating gut immunity when ingested.

| | |
|---|---|
| The powdery crystalline immunomodulating agent in gut prepared in Example 2 comprising the cyclic tetrasaccharide | 40 parts by weight |
| Natural coral powder | 20 parts by weight |
| Calcium lactate | 10 parts by weight |
| Powdery yogurt | 10 parts by weight |
| Guar gum | 12 parts by weight |
| AA2G (L-ascorbic acid 2-glucoside produced by Hayashibara Biochemical Laboratories Inc.) | 3 parts by weight |

-continued

| | |
|---|---|
| αG-HESPERIDIN (transglycosylated hesperidin produced by Hayashibara Biochemical Laboratories Inc.) | 0.5 part by weight |

EXAMPLE 6

Health Food

The following ingredients were blended and made into cheese cracker by conventional way.

| | |
|---|---|
| Wheat flour | 100 parts by weight |
| Fat | 9 parts by weight |
| Malt extract | 1.3 parts by weight |
| Sodium bicarbonate | 0.6 part by weight |
| Cheese powder | 13 parts by weight |
| The syrupy immunomodulating agent in gut prepared in Example 1 comprising the cyclic tetrasaccharide | 2 parts by weight |
| Sucrose | 2 parts by weight |
| Salt | 1 part by weight |
| Ammonium carbonate | 0.6 part by weight |
| Spice | adequate amount |
| Water | 33 parts by weight |

The product has good flavor and can be used as a health food to keep or improve health by modulating gut immunity when ingested.

INDUSTRIAL APPLICABILITY

As described above, routine ingestion of the immunomodulating agent in the gut of the present invention can prevent and treat infections including food poisonings and allergies without adverse side effect by modulating gut immunity. It can be used for keeping and improving health by improvement of enteric environment by increasing good intestinal bacteria such as lactic acid bacteria.

The invention claimed is:

1. A method of treating diseases caused by hepatitis A virus, polio virus, rotavirus, cholera vibrio, dysentery bacillus, typhoid bacteria, *Salmonella, Campyrobacter*, melioidosis bacteria, *Vibrio parahaemolyticus, Brucella*, coliform bacillus O-157, broad tapeworm, "Yokogawakyuchu" (Metagonimus yokogawai), liver flukes, *Echinostomida*, lung flukes, *Anisakis, Gnathostomiasis, Angiostrongylus cantonensis, Entamoeba histolytica, Cryptosporidium, Plasmodium* or microfilaria;

food allergy or pollen allergy, comprising administering to an animal in need thereof an effective amount of a cyclic tetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→}, wherein said diseases are treated by modulating gut immunity.

2. The method according to claim 1 wherein the method accelerates production of at least one of Immunoglobulin A.

3. The method according to claim 1, wherein the method accelerates production of at least one of interferon-γ and transforming growth factor-β.

4. The method according to claim 1 wherein the cyclic tetrasaccharide is administered in food or beverages.

5. The method according to claim 1 wherein the cyclic tetrasaccharide is administered at a dose of 0.001-5 grams/kg. body weight.

* * * * *